United States Patent [19]

Seele et al.

[11] Patent Number: 5,091,401

[45] Date of Patent: Feb. 25, 1992

[54] 1-HALOVINYLAZOLES AND FUNGICIDES CONTAINING THEM

[75] Inventors: Rainer Seele; Reiner Kober, both of Fussgoenheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 546,879

[22] Filed: Jul. 2, 1990

[30] Foreign Application Priority Data

Jul. 13, 1989 [DE] Fed. Rep. of Germany ....... 3923153

[51] Int. Cl.$^5$ ................. A01N 43/653; C07D 249/08
[52] U.S. Cl. .................... 514/383; 514/184; 548/262.2; 548/267.2; 548/268.4
[58] Field of Search ............. 548/101, 268.4, 262.2, 548/267.2; 514/184, 383

[56] References Cited

U.S. PATENT DOCUMENTS 4,213,990 7/1980 Frick et al. .............. 548/262.2
4,495,191 1/1985 Ehrhardt et al. ........... 548/262.2

FOREIGN PATENT DOCUMENTS 060223 9/1982 European Pat. Off. .
0076628 4/1983 European Pat. Off. .
047057 9/1985 European Pat. Off. .
0227100 7/1987 European Pat. Off. .

OTHER PUBLICATIONS

Burger, "Medicinal Chemistry", 2nd ed, N.Y., 1960, p. 1055.

Primary Examiner—Patricia L. Morris
Attorney, Agent, or Firm—Oblon, Spivak, McClelland, Maier & Neustadt

[57] ABSTRACT

1-Halovinylazoles of the general formula

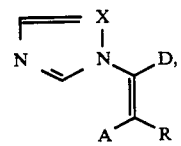

where
A and R are identical or different and are each phenyl, biphenyl, naphthyl or hetaryl, and these radicals are substituted or unsubstituted,
D is chlorine or bromine,
X is CH or N,
and their plant-tolerated acid addition salts and metal complexes, and fungicides containing these compounds.

6 Claims, No Drawings

1-HALOVINYLAZOLES AND FUNGICIDES CONTAINING THEM

The present invention relates to novel azole compounds, processes for their preparation and fungicides containing them.

It is known that 1-(1,2,4-triazol-1-yl)-2-(2-chlorophenyl)-2-(4-fluorophenyl)-ethene (European Patent 47057) can be used as a fungicide. However, the fungicidal actions are not satisfactory in all cases.

We have found that 1-halovinylazoles of the general formula I

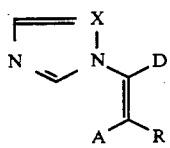

where
- A and R are identical or different and are each phenyl, biphenyl, naphthyl or hetaryl, and these radicals may be monosubstituted to trisubstituted by halogen, nitro, phenoxy, amino, alkyl, alkoxy or haloalkyl, each of 1 to 4 carbon atoms,
- D is chlorine or bromine and
- X is CH or N, and their plant-tolerated acid addition salts or metal complexes have a better fungicidal action than known azole compounds.

The compounds of the formula I contain a polysubstituted double bond and can therefore occur as E/Z isomers. In the case of the novel compounds, the E/Z isomers can be separated in a conventional manner, for example on the basis of their different solubilities or by column chromatography, and the isomers can be isolated in pure form.

Both the individual diastereomers and the mixtures thereof can be used as fungicidal active ingredients.

A and R are identical or different and are each, for example, 1-naphthyl, 2-naphthyl, p-biphenyl, phenyl, halophenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, $C_1$–$C_4$-alkoxyphenyl, 2-methoxyphenyl, 3-methoxyphenyl, 4-methoxyphenyl, 2,4-dimethoxyphenyl, $C_1$–$C_4$-alkylphenyl, 4ethylphenyl, 4-isopropylphenyl, 4-tert-butylphenyl, 4-tertbutoxyphenyl, 2-chloro-4-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, halo-$C_1$–$C_4$-alkylphenyl, 2-trifluoromethylphenyl, 3-trifluoromethylphenyl, 4-trifluoromethylphenyl, pyridyl, 3-pyridyl, furyl, 2-furyl, thienyl, 2-thienyl, 3-thienyl, isoxazolyl or 5-isoxazolyl.

Acid addition salts are, for example, the hydrochlorides, bromides, sulfates, nitrates, phosphates, oxalates or dodecylbenzenesulfonates. The activity of the salts is due to the cation, so that the anion is in general unimportant. The active ingredient salts are prepared by reacting the 1-halovinylazoles (I) with the acids.

Metal complexes of the active ingredients I or of their salts can be formed with, for example, copper, zinc, tin, manganese, iron, cobalt or nickel, by reacting the 1-halovinylazoles with the metal salts.

The compounds of the formula I can be prepared by reacting a compound of the formula II

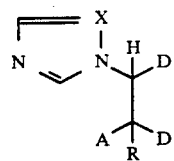

where A, R, D and X have the abovementioned meanings, with a base.

The reaction is carried out in the presence or absence of a solvent or diluent, with the addition of an inorganic or organic base, at from 10° to 120° C.

The preferred solvents and diluents include ketones, such as acetone, methyl ethyl ketone or cyclohexanone, nitriles, such as acetonitrile or propionitrile, alcohols, such as methanol, ethanol, isopropanol, n-butanol or glycol, ethers, such as tetrahydrofuran, diethyl ether, dimethoxyethane, dioxane or diisopropyl ether, amides, such as dimethylformamide, dimethylacetamide or N-methylpyrrolidone, sulfolane and corresponding mixtures.

The reaction is carried out in general at from 20° to 150° C. under atmospheric or superatmospheric pressure, continuously or batchwise.

The starting compounds II can be prepared, for example, by reacting a compound of the formula III

where A, R and D have the abovementioned meanings, with a compound of the formula IV

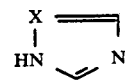

where X has the abovementioned meanings, in the presence of a thionyl halide ($SOD_2$).

The reaction is carried out in the presence or absence of a solvent or diluent at from −30° to 80° C. The preferred solvents and diluents include nitriles, such as acetonitrile or propionitrile, ethers, such as tetrahydrofuran, diethyl ether, dimethoxyethane, dioxane or diisopropyl ether, and in particular hydrocarbons and chlorohydrocarbons, such as pentane, hexane, toluene, methylene chloride, chloroform, carbon tetrachloride or dichloroethane, and corresponding mixtures.

The compounds of the formula II can furthermore be prepared by reacting a compound of the formula V

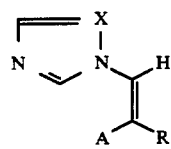

where A, R and X have the abovementioned meanings, with chlorine or bromine in the presence of a Lewis acid, e.g. zinc chloride or zinc bromide.

The reaction is carried out in the presence or absence of a solvent or diluent at from −30° to 100° C. The preferred solvents include esters, such as ethyl acetate, methyl acetate or butyl acetate, ethers, such as tetrahydrofuran, diethyl ether, dimethoxyethane, dioxane or diisopropyl ether, and in particular hydrocarbons and chlorocarbons, such as pentane, hexane, toluene, methylene chloride, chloroform, carbon tetrachloride or dichloroethane, and corresponding mixtures.

Preferred Lewis acids are metal halides, such as zinc chloride, zinc bromide, tin chloride, tin bromide, iron tribromide, aluminum trichloride and titaniun tetrachloride.

The compounds of the formula V can be prepared by known processes (cf. European Patents 60,223 and 47,057).

The Examples which follow illustrate the preparation of the active ingredients.

I. Preparation of the starting materials

Method 1

1,2-Dichloro-1-(1,2,4-triazol-1-yl)-2-(2-fluorophenyl)-2-(4-fluorophenyl)-ethane 1.1 g of zinc chloride are added to a solution of 22.4 g of 1-(1,2,4-triazol-1-yl)-2-(2-fluorophenyl)-2-(4-fluorophenyl)-ethene in 80 ml of carbon tetrachloride, after which 8.4 g of chlorine are passed in in the form of a gas. After the reaction mixture has been stirred for two hours at room temperature (20° C.), the resulting precipitate is filtered off under suction and taken up in methylene chloride, and the solution is washed several times with saturated sodium bicarbonate solution, dried over sodium sulfate and evaporated down. 17.8 g (63%) of 1,2-dichloro-1-(1,2,4-triazol-1-yl)-2-(2-fluorophenyl)-2-(4-fluorophenyl)-ethane are obtained as a 1:1 diastereomer mixture.

II. Preparation of the end products

PREPARATION EXAMPLE 1

1-Chloro-1-(1,2,4-triazol-1-yl)-2-(2-fluorophenyl)-2-(4-fluorophenyl)-ethene (compound No. 1)

5.4 g of sodium methylate are added to a solution of 17.8 g (0.0503 mol) of 1,2-dichloro-1-(1,2,4-triazol-1-yl)-2-(2-fluorophenyl)-2-(4-fluorophenyl)-ethane in 125 ml of methanol. After the reaction mixture has been refluxed for one hour, 100 ml of water are added to the solution, which is then extracted several times by shaking with methyl tert-butyl ether. The organic phase isolated is washed twice with water, dried over sodium sulfate and evaporated down, 15.5 g (97%) of 1-chloro-1-(1,2,4-triazol-1-yl)-2-(2-fluorophenyl)-2-(4-fluorophenyl)-ethane being obtained as a 1:1 E/Z mixture.

The compounds listed in the Table can be prepared similarly to Example 1.

TABLE

| Ex. | A | R | D | X | m.p./IR | Isomer |
|---|---|---|---|---|---|---|
| 1 | 4-F—C$_6$H$_4$ | 2-F—C$_6$H$_4$ | Cl | N | 1603, 1508, 1276, 1233, 759 cm$^{-1}$ | E/Z = 1:1 |
| 2 | 4-F—C$_6$H$_4$ | 2-F—C$_6$H$_4$ | Cl | CH | | |
| 3 | 4-F—C$_6$H$_4$ | 2-F—C$_6$H$_4$ | Br | N | resin | E/Z = 1:1 |
| 4 | 4-F—C$_6$H$_4$ | 2-F—C$_6$H$_4$ | Br | CH | | |
| 5 | 4-F—C$_6$H$_4$ | 3-F—C$_6$H$_4$ | Cl | N | | |
| 6 | 4-F—C$_6$H$_4$ | 4-F—C$_6$H$_4$ | Cl | N | 122–125° C. | — |
| 7 | 4-F—C$_6$H$_4$ | 4-F—C$_6$H$_4$ | Cl | CH | | |
| 8 | 4-F—C$_6$H$_4$ | 4-F—C$_6$H$_4$ | Br | N | | |
| 9 | 4-F—C$_6$H$_4$ | 4-F—C$_6$H$_4$ | Br | CH | | |
| 10 | 4-F—C$_6$H$_4$ | C$_6$H$_5$ | Cl | N | 1604, 1507, 1270, 1231 1132, 846, 699 cm$^{-1}$ | E/Z = 1:1 |
| 11 | 4-F—C$_6$H$_4$ | C$_6$H$_5$ | Br | N | | |
| 12 | 4-F—C$_6$H$_4$ | C$_6$H$_5$ | Cl | CH | | |
| 13 | 4-F—C$_6$H$_4$ | 2-Cl—C$_6$H$_4$ | Cl | N | 1602, 1507, 1276, 1234 753 cm$^{-1}$ | E/Z = 1:1 |
| 14 | 4-F—C$_6$H$_4$ | 2-Cl—C$_6$H$_4$ | Cl | CH | | |
| 15 | 4-F—C$_6$H$_4$ | 2-Cl—C$_6$H$_4$ | Br | N | | |
| 16 | 4-F—C$_6$H$_4$ | 2-Cl—C$_6$H$_4$ | Br | CH | | |
| 17 | 4-F—C$_6$H$_4$ | 3-Cl—C$_6$H$_4$ | Cl | N | | |
| 18 | 4-F—C$_6$H$_4$ | 4-Cl—C$_6$H$_4$ | Cl | N | | |
| 19 | 4-F—C$_6$H$_4$ | 4-Cl—C$_6$H$_4$ | Br | N | | |
| 20 | 4-F—C$_6$H$_4$ | 4-Cl—C$_6$H$_4$ | Cl | CH | | |
| 21 | 4-F—C$_6$H$_4$ | 2-Br—C$_6$H$_4$ | Cl | N | | |
| 22 | 4-F—C$_6$H$_4$ | p-biphenyl | Cl | N | | |
| 23 | 4-F—C$_6$H$_4$ | 2-naphthyl | Cl | N | | |
| 24 | 4-F—C$_6$H$_4$ | 1-naphthyl | Cl | N | | |
| 25 | 4-F—C$_6$H$_4$ | 2-CH$_3$—C$_6$H$_4$ | Cl | N | | |
| 26 | 4-F—C$_6$H$_4$ | 2-CH$_3$—C$_6$H$_4$ | Br | N | | |
| 27 | 4-F—C$_6$H$_4$ | 2-CH$_3$—C$_6$H$_4$ | Cl | CH | | |
| 28 | 4-F—C$_6$H$_4$ | 4-CH$_3$—C$_6$H$_4$ | Cl | N | | |
| 29 | 4-F—C$_6$H$_4$ | 2,4-di-CH$_3$—C$_6$H$_3$ | Cl | N | | |
| 30 | 4-F—C$_6$H$_4$ | 2-CF$_3$—C$_6$H$_4$ | Cl | N | | |
| 31 | 4-F—C$_6$H$_4$ | 2-CF$_3$—C$_6$H$_4$ | Br | N | | |
| 32 | 4-F—C$_6$H$_4$ | 2-CF$_3$—C$_6$H$_4$ | Cl | CH | | |
| 33 | 4-F—C$_6$H$_4$ | 3-CF$_3$—C$_6$H$_4$ | Cl | N | | |
| 34 | 4-F—C$_6$H$_4$ | 4-CF$_3$—C$_6$H$_4$ | Cl | N | | |
| 35 | 4-F—C$_6$H$_4$ | 4-CF$_3$—C$_6$H$_4$ | Br | N | | |
| 36 | 4-F—C$_6$H$_4$ | 4-CF$_3$—C$_6$H$_4$ | Cl | CH | | |
| 37 | 4-F—C$_6$H$_4$ | 3-NO$_2$—C$_6$H$_4$ | Cl | N | | |
| 38 | 4-F—C$_6$H$_4$ | 3-NH$_2$—C$_6$H$_4$ | Cl | N | | |
| 39 | 4-F—C$_6$H$_4$ | 2-OCH$_3$—C$_6$H$_4$ | Cl | N | | |
| 40 | 4-F—C$_6$H$_4$ | 2-OCH$_3$—C$_6$H$_4$ | Br | N | | |
| 41 | 4-F—C$_6$H$_4$ | 2-OCH$_3$—C$_6$H$_4$ | Cl | CH | | |

TABLE-continued

| Ex. | A | R | D | X | m.p./IR | Isomer |
|---|---|---|---|---|---|---|
| 42 | 4-F—C$_6$H$_4$ | 3-OCH$_3$—C$_6$H$_4$ | Cl | N | | |
| 43 | 4-F—C$_6$H$_4$ | 3-OCH$_3$—C$_6$H$_4$ | Br | N | | |
| 44 | 4-F—C$_6$H$_4$ | 4-OCH$_3$—C$_6$H$_4$ | Cl | N | | |
| 45 | 4-F—C$_6$H$_4$ | 4-OCH$_3$—C$_6$H$_4$ | Br | N | | |
| 46 | 4-F—C$_6$H$_4$ | 4-OCH$_3$—C$_6$H$_4$ | Cl | CH | | |
| 47 | 4-F—C$_6$H$_4$ | 2-pyridyl | Cl | N | | |
| 48 | 4-F—C$_6$H$_4$ | 3-pyridyl | Cl | N | | |
| 49 | 4-F—C$_6$H$_4$ | 4-pyridyl | Cl | N | | |
| 50 | 4-F—C$_6$H$_4$ | 2-thienyl | Cl | N | | |
| 51 | 4-F—C$_6$H$_4$ | 3-thienyl | Cl | N | | |
| 52 | 4-F—C$_6$H$_4$ | 2-furyl | Cl | N | | |
| 53 | 4-F—C$_6$H$_4$ | 5-isoxazolyl | Cl | N | | |
| 54 | C$_6$H$_5$ | 2-F—C$_6$H$_4$ | Cl | N | | |
| 55 | C$_6$H$_5$ | C$_6$H$_5$ | Cl | N | | |
| 56 | C$_6$H$_5$ | 2-Cl—C$_6$H$_4$ | Cl | N | 1502, 1402, 1275, 1132, 857, 756, 699 cm$^{-1}$ | E/Z = 1:1 |
| 57 | C$_6$H$_5$ | 4-Cl—C$_6$H$_4$ | Cl | N | resin | E/Z = 1:1 |
| 58 | C$_6$H$_5$ | 2-Br—C$_6$H$_4$ | Cl | N | | |
| 59 | C$_6$H$_5$ | 4-Br—C$_6$H$_4$ | Cl | N | | |
| 60 | C$_6$H$_5$ | 2-CH$_3$—C$_6$H$_4$ | Cl | N | | |
| 61 | C$_6$H$_5$ | 4-CH$_3$—C$_6$H$_4$ | Cl | N | | |
| 62 | C$_6$H$_5$ | 4-tert.-C$_4$H$_9$—C$_6$H$_4$ | Cl | N | | |
| 63 | C$_6$H$_5$ | 2-CF$_3$—C$_6$H$_4$ | Cl | N | | |
| 64 | C$_6$H$_5$ | 4-CF$_3$—C$_6$H$_4$ | Cl | N | | |
| 65 | C$_6$H$_5$ | 2-OCH$_3$—C$_6$H$_4$ | Cl | N | | |
| 66 | C$_6$H$_5$ | 4-OCH$_3$—C$_6$H$_4$ | Cl | N | | |
| 67 | C$_6$H$_5$ | 2-naphthyl | Cl | N | | |
| 68 | C$_6$H$_5$ | 2-pyridyl | Cl | N | | |
| 69 | C$_6$H$_5$ | 3-pyridyl | Cl | N | | |
| 70 | C$_6$H$_5$ | 2-thienyl | Cl | N | | |
| 71 | C$_6$H$_5$ | 3-thienyl | Cl | N | | |
| 72 | 4-Cl—C$_6$H$_4$ | 2-F—C$_6$H$_4$ | Cl | N | | |
| 73 | 4-Cl—C$_6$H$_4$ | 2-Cl—C$_6$H$_4$ | Cl | N | | |
| 74 | 4-Cl—C$_6$H$_4$ | 4-Cl—C$_6$H$_4$ | Cl | N | 1598, 1491, 1275, 1092, 1015, 795, cm$^{-1}$ | — |
| 75 | 4-Cl—C$_6$H$_4$ | 2-Br—C$_6$H$_4$ | Cl | N | | |
| 76 | 4-Cl—C$_6$H$_4$ | 4-Br—C$_6$H$_4$ | Cl | N | | |
| 77 | 4-Cl—C$_6$H$_4$ | 2-CH$_3$—C$_6$H$_4$ | Cl | N | | |
| 78 | 4-Cl—C$_6$H$_4$ | 4-CH$_3$—C$_6$H$_4$ | Cl | N | | |
| 79 | 4-Cl—C$_6$H$_4$ | 2-CF$_3$—C$_6$H$_4$ | Cl | N | | |
| 80 | 4-Cl—C$_6$H$_4$ | 4-CF$_3$—C$_6$H$_4$ | Cl | N | | |
| 81 | 4-Cl—C$_6$H$_4$ | 2-OCH$_3$—C$_6$H$_4$ | Cl | N | | |
| 82 | 4-Cl—C$_6$H$_4$ | 4-OCH$_3$—C$_6$H$_4$ | Cl | N | | |
| 83 | 4-Br—C$_6$H$_4$ | 2-F—C$_6$H$_4$ | Cl | N | | |
| 84 | 4-Br—C$_6$H$_4$ | 2-Cl—C$_6$H$_4$ | Cl | N | | |
| 85 | 4-Br—C$_6$H$_4$ | 2-CH$_3$—C$_6$H$_4$ | Cl | N | | |
| 86 | 4-Br—C$_6$H$_4$ | 2-CF$_3$—C$_6$H$_4$ | Cl | N | | |
| 87 | 4-Br—C$_6$H$_4$ | 4-CF$_3$—C$_6$H$_4$ | Cl | N | | |
| 88 | 4-Br—C$_6$H$_4$ | 2-OCH$_3$—C$_6$H$_4$ | Cl | N | | |
| 89 | 4-Br—C$_6$H$_4$ | 4-OCH$_3$—C$_6$H$_4$ | Cl | N | | |
| 90 | 4-CH$_3$—C$_6$H$_4$ | 2-Cl—C$_6$H$_4$ | Cl | N | | |
| 91 | 4-CH$_3$—C$_6$H$_4$ | 2-F—C$_6$H$_4$ | Cl | N | | |
| 92 | 4-CH$_3$—C$_6$H$_4$ | 2-CH$_3$—C$_6$H$_4$ | Cl | N | | |
| 93 | 4-CH$_3$—C$_6$H$_4$ | 4-CH$_3$—C$_6$H$_4$ | Cl | N | | |
| 94 | 4-CH$_3$—C$_6$H$_4$ | 2-CF$_3$—C$_6$H$_4$ | Cl | N | | |
| 95 | 4-CH$_3$—C$_6$H$_4$ | 4-CF$_3$—C$_6$H$_4$ | Cl | N | | |
| 96 | 4-CH$_3$—C$_6$H$_4$ | 2-OCH$_3$—C$_6$H$_4$ | Cl | N | | |
| 97 | 4-CH$_3$—C$_6$H$_4$ | 4-OCH$_3$—C$_6$H$_4$ | Cl | N | | |
| 98 | 4-CF$_3$—C$_6$H$_4$ | 2-Cl—C$_6$H$_4$ | Cl | N | | |
| 99 | 4-CF$_3$—C$_6$H$_4$ | 2-F—C$_6$H$_4$ | Cl | N | | |
| 100 | 4-CF$_3$—C$_6$H$_4$ | 2-CH$_3$—C$_6$H$_4$ | Cl | N | | |
| 101 | 4-CF$_3$—C$_6$H$_4$ | 2-CF$_3$—C$_6$H$_4$ | Cl | N | | |
| 102 | 4-CF$_3$—C$_6$H$_4$ | 2-OCH$_3$—C$_6$H$_4$ | Cl | N | | |
| 103 | 4-OCH$_3$—C$_6$H$_4$ | 2-Cl—C$_6$H$_4$ | Cl | N | | |
| 104 | 4-OCH$_3$—C$_6$H$_4$ | 2-F—C$_6$H$_4$ | Cl | N | | |
| 105 | 4-OCH$_3$—C$_6$H$_4$ | 2-CH$_3$—C$_6$H$_4$ | Cl | N | | |
| 106 | 4-OCH$_3$—C$_6$H$_4$ | 2-CF$_3$—C$_6$H$_4$ | Cl | N | | |
| 107 | 4-OCH$_3$—C$_6$H$_4$ | 2-OCH$_3$—C$_6$H$_4$ | Cl | N | | |
| 108 | 4-OCH$_3$—C$_6$H$_4$ | 4-OCH$_3$—C$_6$H$_4$ | Cl | N | | |
| 109 | 2-F—C$_6$H$_4$ | 2-Cl—C$_6$H$_4$ | Cl | N | | |
| 110 | 2-F—C$_6$H$_4$ | 2-F—C$_6$H$_4$ | Cl | N | | |
| 111 | 2-F—C$_6$H$_4$ | 2-CH$_3$—C$_6$H$_4$ | Cl | N | | |
| 112 | 2-Cl—C$_6$H$_4$ | 2-CH$_3$—C$_6$H$_4$ | Cl | N | | |
| 113 | 2-Cl—C$_6$H$_4$ | 2-CF$_3$—C$_6$H$_4$ | Cl | N | | |
| 114 | 2-Cl—C$_6$H$_4$ | 2-OCH$_3$—C$_6$H$_4$ | Cl | N | | |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in vegetables and fruit.

The compounds are applied by spraying or dusting the plants with the active ingredients, or treating the seeds of the plants with the active ingredients. They may be applied before or after infection of the plants or seeds by the fungi. Either the fungi themselves, or the plants, seeds, materials or soil to be protected against fungal attack are treated with a fungicidally effective amount of the active ingredient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials (wood), for example against Paecilomyces variotii.

When the active ingredients are used for treating seed, amounts of from 0.001 to 50, and preferably from 0.01 to 10, g per kg of seed are usually employed.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 6 is mixed with 10 parts by weight of N-methyl-α-pyrrolidone. A mixture is obtained which is suitable for application in the form of very fine drops.

II. 20 parts by weight of compound no. 13 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 6 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 13 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 6 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 13 is intimately mixed with 97 parts by weight of particulate kaolin. A dust is obtained containing 3% by weight of the active ingredient.

VII. 30 parts by weight of compound no. 6 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 13 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 6 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLE

The active ingredient 1-(1,2,4-triazol-1-yl)-2-(2-chlorophenyl)-2-(4-fluorophenyl)-ethene (A) disclosed in EP 47,057 was used for comparison purposes Action on wheat brown rust Leaves of pot-grown wheat seedlings of the "Frühgold" variety were dusted with spores of brown rust (Puccinia recondita). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 6 and 13, applied as 0.025 wt % spray liquors, have a better fungicidal action (94%) than prior art comparative agent A (55%).

We claim:

1. A compound selected from the group consisting of those of the formula I

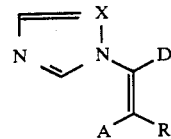

wherein A is 4-fluorophenyl and R is selected from the group consisting of phenyl, substituted phenyl, biphenylyl, substituted biphenylyl, naphthyl, and substituted naphthyl, wherein the substituents are 1 to 3 substituents selected from the group consisting of halo, nitro, phenoxy, amino, alkyl of 1 to 4 carbon atoms, alkoxy of 1 to 4 carbon atoms, and haloalkyl of 1 to 4 carbon atoms;

D is selected from the group consisting of chloro and bromo; and

X is N;

a plant tolerated acid addition salt thereof, and a metal complex thereof.

2. A fungicidal composition containing a carrier and a fungicidally effective amount of a compound of claim 1.

3. A process for combatting fungi wherein the fungi or the plant materials, plant areas, plants or seeds which are threatened by fungus attack are contacted with a fungicidally effective amount of a compound of claim 1.

4. A compound of the formula

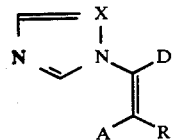

wherein A is 4-fluorophenyl and R is selected from the group consisting of 2-fluorophenyl, 4-fluorophenyl, and 2-chlorophenyl, D is chloro or bromo, and X is N, or a plant tolerated acid addition salt or metal complex thereof.

5. A compound of the formula I as set forth in claim 1, wherein D is Cl and R is 4-fluorophenyl.

6. A compound of the formula I as set forth in claim 1, wherein D is Cl and R is 2-chlorophenyl.

* * * * *